(12) United States Patent
Focht et al.

(10) Patent No.: US 12,349,990 B2
(45) Date of Patent: Jul. 8, 2025

(54) ROBOTIC SURGICAL INSTRUMENT CHASSIS

(71) Applicant: CMR SURGICAL LIMITED, Cambridge (GB)

(72) Inventors: Kenneth Focht, Needham, MA (US); Joseph Gordon, Mansfield, MA (US)

(73) Assignee: CMR SURGICAL LIMITED, Cambridge (GB)

( * ) Notice: Subject to any disclaimer, the term of this patent is extended or adjusted under 35 U.S.C. 154(b) by 794 days.

(21) Appl. No.: 17/400,746

(22) Filed: Aug. 12, 2021

(65) Prior Publication Data
US 2022/0104891 A1    Apr. 7, 2022

(30) Foreign Application Priority Data
Oct. 7, 2020   (GB) .................................... 2015913

(51) Int. Cl.
*A61B 34/30*   (2016.01)
*A61B 34/00*   (2016.01)

(52) U.S. Cl.
CPC .............. *A61B 34/30* (2016.02); *A61B 34/71* (2016.02); *A61B 2034/715* (2016.02)

(58) Field of Classification Search
CPC ... A61B 34/30; A61B 34/71; A61B 2034/715; A61B 2034/301; A61B 2034/302; A61B 2034/305; A61B 2034/306; A61B 34/70
See application file for complete search history.

(56) References Cited

U.S. PATENT DOCUMENTS

| 2015/0265355 A1 | 9/2015 | Prestel et al. |
| 2019/0223960 A1* | 7/2019 | Chaplin ................. A61B 34/30 |
| 2020/0197110 A1 | 6/2020 | Marshall |

FOREIGN PATENT DOCUMENTS

| GB | 2563233 A | 12/2018 |
| GB | 2570518 A | 7/2019 |
| WO | 2017098273 A1 | 6/2017 |
| WO | 2019222058 A1 | 11/2019 |

OTHER PUBLICATIONS

International Search Report and the Written Opinion of the International Searching Authority from corresponding PCT/GB2021/052584 dated Dec. 20, 2021.
United Kingdom Search Report from corresponding United Kingdom Application No. GB2015913.3 dated Mar. 19, 2021.

* cited by examiner

*Primary Examiner* — Tan-Uyen T Ho
*Assistant Examiner* — Bridget E. Rabaglia
(74) *Attorney, Agent, or Firm* — Lando & Anastasi, LLP

(57) ABSTRACT

A robotic surgical instrument comprising: a shaft; driving elements running through the shaft; an articulation at a distal end of the shaft for articulating an end effector, the articulation driveable by the driving elements; and an instrument interface at a proximal end of the shaft for driving the driving elements, the instrument interface comprising: a monocoque chassis; and a routing pulley component housed by the monocoque chassis and separable from the monocoque chassis; wherein the instrument interface is configured to be assembled by: routing the driving elements from the shaft around pulleys of the routing pulley component; securing the driving elements to the monocoque chassis; and after the routing and securing steps, placing the routing pulley component into the monocoque chassis.

19 Claims, 12 Drawing Sheets

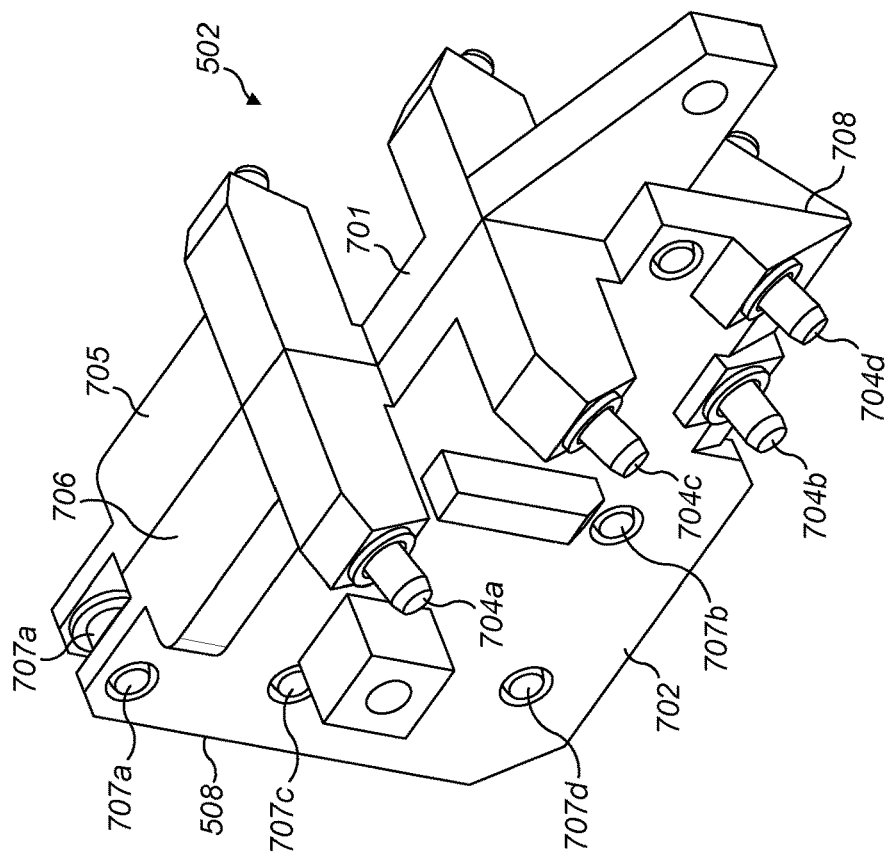
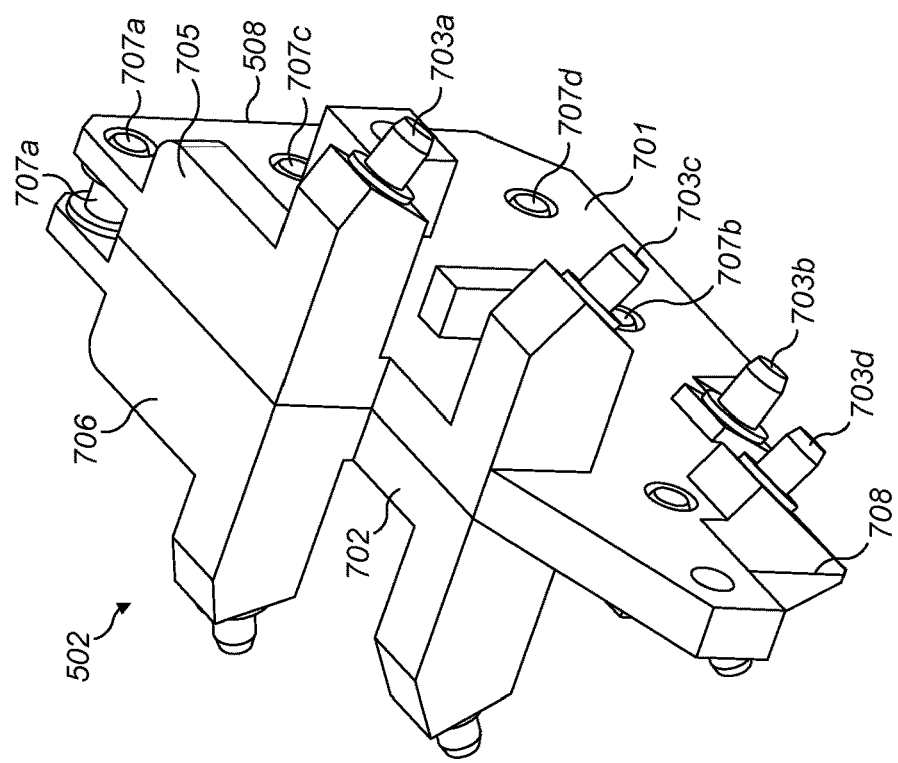
FIG. 7b
FIG. 7a

ROBOTIC SURGICAL INSTRUMENT CHASSIS

CROSS-REFERENCE TO RELATED APPLICATION

This application claims the benefit under 35 U.S.C. § 119 of United Kingdom Patent Application No. 2015913.3 filed on Oct. 7, 2020 which is hereby incorporated herein by reference in its entirety for all purposes.

BACKGROUND

It is known to use robots for assisting and performing surgery. FIG. 1 illustrates a typical surgical robotic system. A surgical robot 100 consists of a base 102, an arm 104 and an instrument 106. The base supports the robot, and may itself be attached rigidly to, for example, the operating theatre floor, the operating theatre ceiling or a cart. The arm extends between the base and the instrument. The arm is articulated by means of multiple flexible joints 108 along its length, which are used to locate the surgical instrument in a desired location relative to the patient.

A surgeon controls the surgical robot 100 via a remote surgeon console 112. The surgeon console comprises one or more surgeon input devices 114. These may take the form of a hand controller or foot pedal. The surgeon console also comprises a display 116.

A control system 118 connects the surgeon console 112 to the surgical robot 100. The control system receives inputs from the surgeon input device(s) 114 and converts these to control signals to move the joints of the robot arm 104 and instrument 106. The control system sends these control signals to the robot, where the corresponding joints are driven accordingly.

The surgical instrument 106 is attached to the distal end of the robot arm. The surgical instrument penetrates the body of the patient at a port so as to access the surgical site. The surgical instrument comprises a shaft connected to a distal end effector 110 by a jointed articulation. The end effector engages in a surgical procedure.

At the other end of the shaft, an instrument interface is connected to a drive assembly interface of the arm, thereby connecting the instrument to the arm. Mechanical drive is transferred from the drive assembly of the arm to the instrument through these interfaces. Typically, the instrument is cable driven. Thus, the instrument interface houses cables which feed through the shaft to drive the joints of the articulation for moving the end effector. Those cables are driven by the drive assembly through the drive assembly/instrument interface.

The articulation may comprise several joints each of which may be driven by a separate cable loop. Thus, when manufacturing the instrument, several cable loops need to be assembled into the instrument interface. To achieve this, it is known to use a two-part instrument interface chassis. A first set of cables and routing components are assembled in one part of the chassis, whilst another set of cables and routing components are assembled in the other part of the chassis. The two component chassis parts are then assembled together. As well as an awkward assembly process, the two component parts of the chassis flex with respect to each other during use of the instrument thereby reducing the efficiency of the drive transfer from the robot arm to the end effector.

There is thus a need for an instrument interface that is simpler to assemble and provides more efficient mechanical drive to the end effector.

SUMMARY OF THE INVENTION

According to an aspect of the invention, there is provided a robotic surgical instrument comprising: a shaft; driving elements running through the shaft; an articulation at a distal end of the shaft for articulating an end effector, the articulation driveable by the driving elements; and an instrument interface at a proximal end of the shaft for driving the driving elements, the instrument interface comprising: a monocoque chassis; and a routing pulley component housed by the monocoque chassis and separable from the monocoque chassis; wherein the instrument interface is configured to be assembled by: routing the driving elements around pulleys of the routing pulley component; securing the driving elements to the monocoque chassis; and placing the routing pulley component into the monocoque chassis.

The routing pulley component and monocoque chassis may be shaped and sized such that the routing pulley component push fits into the monocoque chassis.

The routing pulley component may be secured to the monocoque chassis by a single fixing only.

The routing pulley component may comprise a first external face, the first external face comprising a first set of pulleys for constraining a first driving element, wherein a first joint of the articulation is driveable by the first driving element.

The first set of pulleys may be aligned in a first plane such that the first driving element lies in the first plane.

The routing pulley component may comprise a second external face, the second external face comprising a second set of pulleys for constraining a second driving element, wherein a second joint of the articulation is driveable by the second driving element.

The second set of pulleys may be aligned in a second plane such that the second driving element lies in the second plane.

The routing pulley component may comprise: a first section comprising the first external face; and a second section comprising the second external face; wherein the first section and second section are separable from each other.

The first section may comprise a first inner face opposing the first external face; and the second section may comprise a second inner face opposing the second external face; the first and second inner faces being joinable together so as to provide a third set of pulleys for constraining a third driving element, wherein a third joint of the articulation is driveable by the third driving element.

The third set of pulleys may be aligned in a third plane such that the third driving element lies in the third plane.

The monocoque chassis may comprise instrument interface elements, each instrument interface element being exposed at the exterior of the instrument interface so as to be driveable by a drive assembly external to the instrument interface, each driving element terminating at a corresponding instrument interface element.

The instrument interface element corresponding to a driving element may lie in the same plane as the set of pulleys which constrains that driving element.

For each driving element, the monocoque chassis may comprise a single pulley only for constraining that driving element, the single pulley moveable so as to tension the driving element.

The shaft may be rigidly secured to the monocoque chassis.

According to an aspect of the invention, there is provided a method of assembling a robotic surgical instrument, the robotic surgical instrument comprising a shaft, driving elements, an articulation at the distal end of the shaft for articulating an end effector, the articulation driveable by the driving elements, and an instrument interface at a proximal end of the shaft for driving the driving elements, the instrument interface comprising a monocoque chassis and a routing pulley component separable from the monocoque chassis, the method comprising: routing the driving elements around pulleys of the routing pulley component; securing the driving elements to the monocoque chassis; and placing the routing pulley component into the monocoque chassis.

The routing step may comprise: routing a first driving element around a first external face of the routing pulley component; and routing a second driving element around a second external face of the routing pulley component.

The routing pulley component may comprise a first section and a second section, the first section comprising the first external face and a first inner face opposing the first external face, and the second section comprising the second external face and a second inner face opposing the second external face, wherein the first section and second section are separable from each other. The routing step may comprise: routing a third driving element around the first inner face of the first section; and joining the first and second sections together by joining the second inner face of the second section to the first inner face of the first section so as to constrain the third driving element about a set of pulleys provided by the joining together of the first and second sections.

Placing the routing pulley component into the monocoque chassis may comprise push-fitting the routing component into the monocoque chassis.

The method may further comprise securing the routing pulley component into the monocoque chassis by a single fixing only.

For each driving element, the monocoque chassis may comprise a single pulley only for constraining that driving element, and the method may further comprise tensioning each driving element by displacing the single pulley.

BRIEF DESCRIPTION OF THE FIGURES

The present invention will now be described by way of example with reference to the accompanying drawings. In the drawings:

FIGS. 7a and 7b illustrate a routing pulley component of the instrument interface;

DETAILED DESCRIPTION

Figure 1:
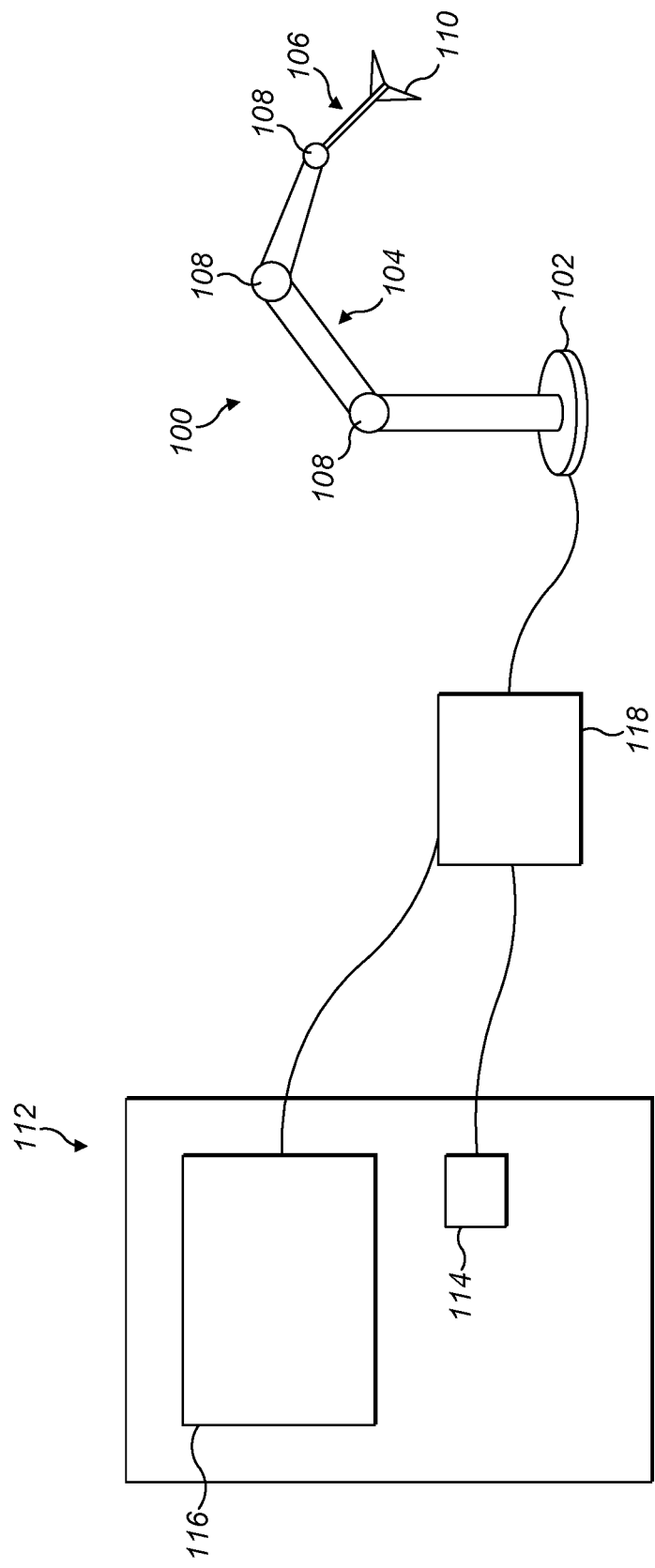
FIG. 1 illustrates a surgical robot system for performing a surgical procedure.

The following describes a surgical instrument, and in particular the interface by which the surgical instrument connects to a surgical robotic arm. The surgical robotic arm and surgical instrument form part of a surgical robotic system of the type illustrated in FIG. 1.

Figure 2:
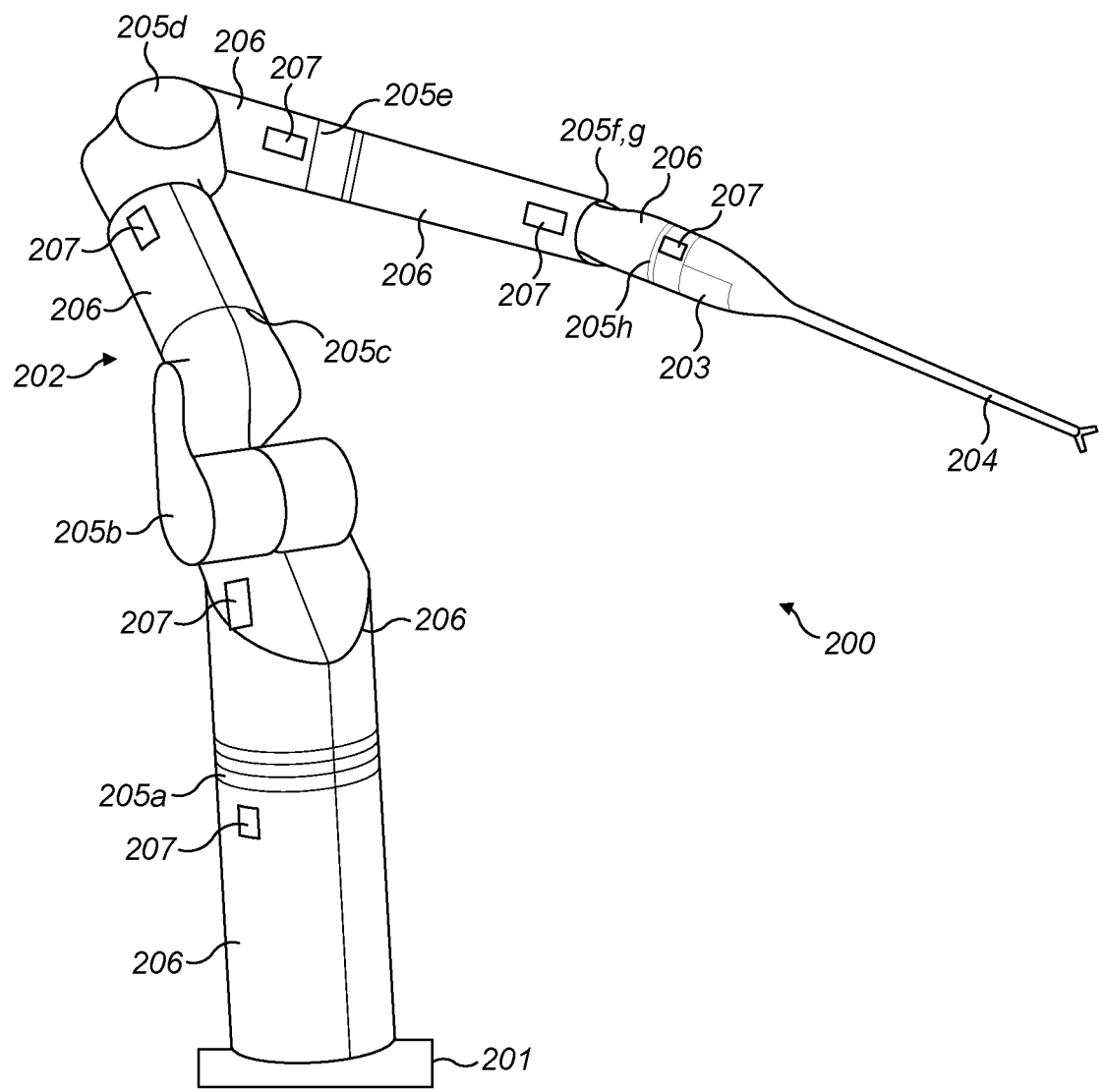
FIG. 2 illustrates a surgical robot.

FIG. 2 illustrates an example robot 200. The robot comprises a base 201 which is fixed in place when a surgical procedure is being performed. Suitably, the base 201 is mounted to a chassis. That chassis may be a cart, for example a bedside cart for mounting the robot at bed height. Alternatively, the chassis may be a ceiling mounted device, or a bed mounted device.

A robot arm 202 extends from the base 201 of the robot to a terminal link 203 to which a surgical instrument 204 can be attached. The arm is flexible. It is articulated by means of multiple flexible joints 205 along its length. In between the joints are rigid arm links 206. The arm in FIG. 2 has eight joints. The joints include one or more roll joints (which have an axis of rotation along the longitudinal direction of the arm members on either side of the joint), one or more pitch joints (which have an axis of rotation transverse to the longitudinal direction of the preceding arm member), and one or more yaw joints (which also have an axis of rotation transverse to the longitudinal direction of the preceding arm member and also transverse to the rotation axis of a co-located pitch joint). In the example of FIG. 2: joints 205a, 205c, 205e and 205h are roll joints; joints 205b, 205d and 205f are pitch joints; and joint 205g is a yaw joint. Pitch joint 205f and yaw joint 205g have intersecting axes of rotation. The order of the joints from the base 201 to the terminal link 203 of the robot arm is thus: roll, pitch, roll, pitch, roll, pitch, yaw, roll. However, the arm could be jointed differently. For example, the arm may have fewer than eight or more than eight joints. The arm may include joints that permit motion other than rotation between respective sides of the joint, for example a telescopic joint. The robot comprises a set of drivers 207. Each driver 207 has a motor which drives one or more of the joints 205. The terminal link 203 of the robot arm comprises a drive assembly for interfacing and driving a surgical instrument.

Figure 3:
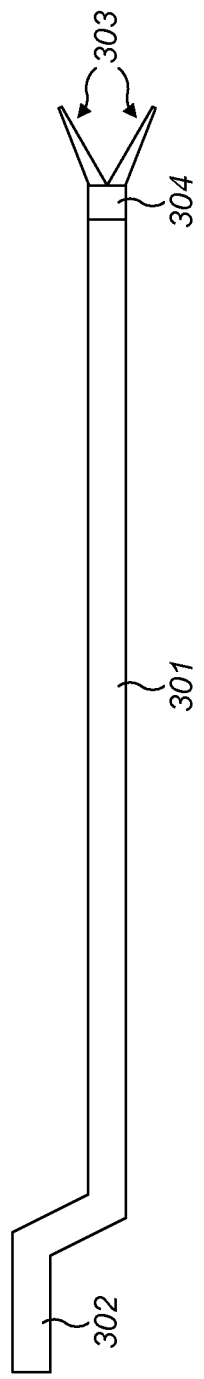
FIG. 3 illustrates an exemplary surgical instrument.

FIG. 3 illustrates a surgical instrument 204. The surgical instrument has an elongate profile, with a shaft 301 spanning between its proximal end which is attached to the robot arm and its distal end which accesses the surgical site within the patient body. Suitably, the shaft is rigid. The shaft may be straight. The proximal end of the surgical instrument and the instrument shaft may be rigid with respect to each other and rigid with respect to the distal end of the robot arm when attached to it. At the proximal end of the instrument, the shaft 301 is connected to an instrument interface 302. The instrument interface engages with a drive assembly interface at the distal end of the robot arm. At the distal end of the surgical instrument, the distal end of the shaft is connected to an end effector 303 by an articulation 304. The end effector 303 engages in a surgical procedure at the surgical site. The end effector may take any suitable form. For example, the end effector could be a pair of curved scissors, an electrosurgical instrument such as a pair of monopolar scissors, a needle holder, a pair of jaws, or a fenestrated grasper.

Figure 4A:
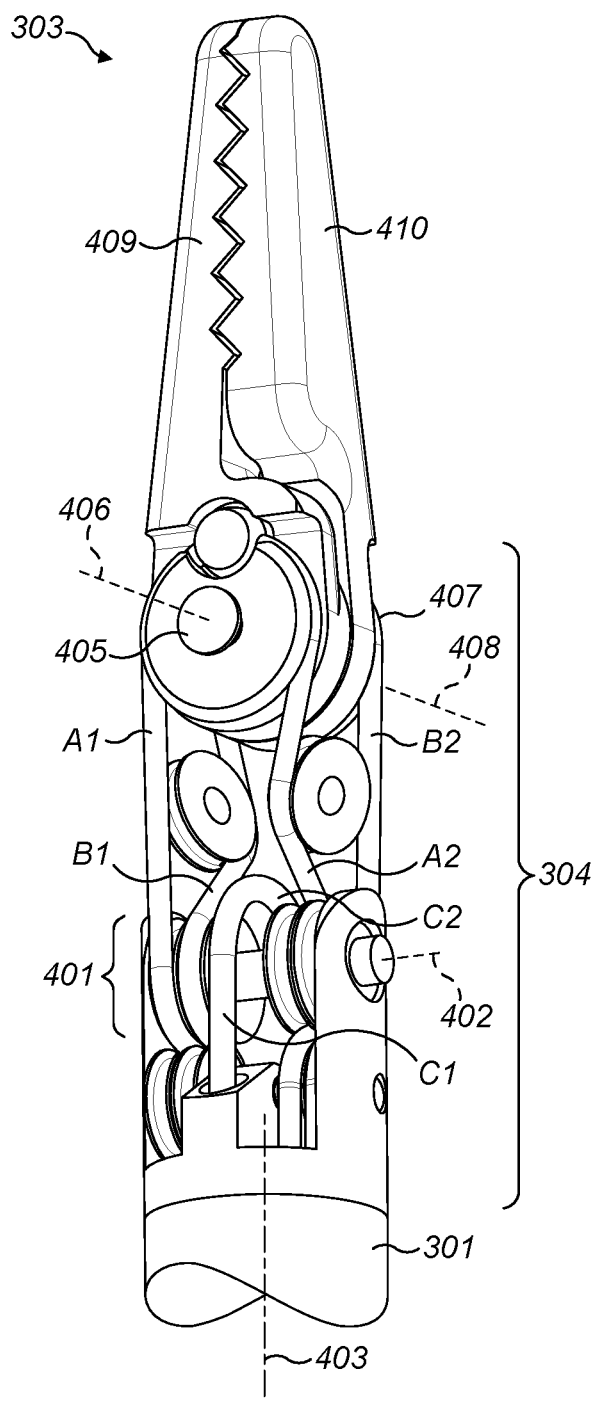
FIGS. 4a and 4b illustrate the distal end of an exemplary surgical instrument.
Figure 4B:
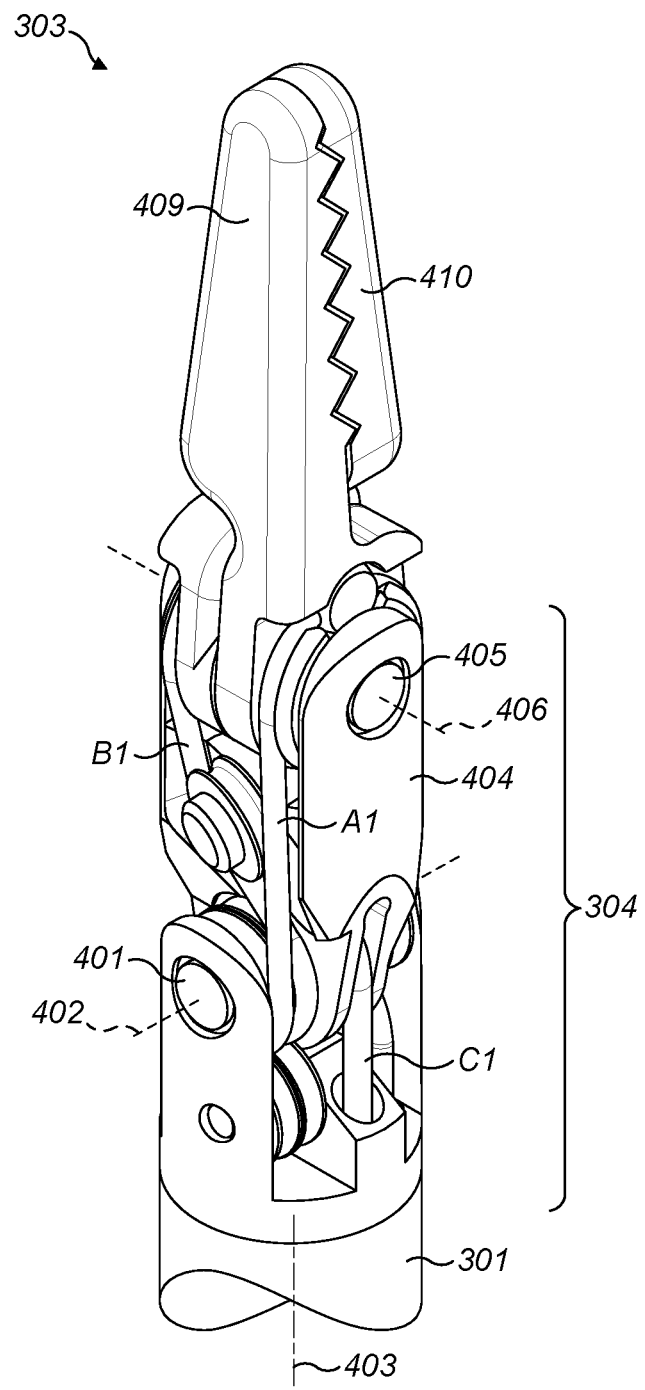

FIGS. 4a and 4b illustrate the distal end of an exemplary instrument which has a pair of jaws as the end effector 303.

The shaft 301 is connected to the end effector 303 by articulation 304. The articulation 304 comprises several joints. These joints enable the pose of the end effector to be altered relative to the direction of the instrument shaft. Although not shown in FIGS. 4a and 4b, the end effector may also comprise joint(s). In the example of FIGS. 4a and 4b, the articulation 304 comprises a pitch joint 401. The pitch joint 401 rotates about pitch axis 402, which is perpendicular to the longitudinal axis 403 of the shaft 301. The pitch joint 401 permits a supporting body 404 (described below) and hence the end effector 303 to rotate about the pitch axis 402 relative to the shaft. In the example of FIGS. 4a and 4b, the articulation also comprises a first yaw joint 405 and a second yaw joint 407. First yaw joint 405 rotates about first yaw axis 406. Second yaw joint 407 rotates about second yaw axis 408. Both yaw axes 406 and 408 are perpendicular to pitch axis 402. Yaw axes 406 and 408 may be parallel. Yaw axes 406 and 408 may be collinear. The articulation 304 comprises a supporting body 404. At one end, the supporting body 404 is connected to the shaft 301 by pitch joint 401. At its other end, the supporting body 404 is connected to the end effector 303 by the yaw joints 405 and 407. This supporting body is omitted from FIG. 4a for ease of illustration so as to enable the other structure of the articulation to be more easily seen.

The end effector 303 shown comprises two end effector elements 409, 410. Alternatively, the end effector may have a single end effector element. The end effector elements 409, 410 shown in FIGS. 4a and 4b are opposing jaws. However, the end effector elements may be any type of opposing end effector elements. The first yaw joint 405 is fast with the first end effector element 409 and permits the first end effector element 409 to rotate about the first yaw axis 406 relative to the supporting body 404 and the pitch joint 401. The second yaw joint 407 is fast with the second end effector element 410 and permits the second end effector element 410 to rotate about the second yaw axis 408 relative to the supporting body 404 and the pitch joint 401. In FIGS. 4a and 4b, the end effector elements 409, 410 are shown in a closed configuration in which the jaws abut.

The joints illustrated in FIGS. 4a and 4b are driven by pairs of driving elements. The driving elements are elongate. They are flexible transverse to their longitudinal extent. They resist compression and tension forces along their longitudinal extent. A first pair of driving elements A1, A2 are constrained to move around the first yaw joint 405. Driving elements A1, A2 drive rotation of the first end effector element 409 about the first yaw axis 406. FIGS. 4a and 4b illustrate a second pair of driving elements B1, B2 which are constrained to move around the second yaw joint 407. Driving elements B1, B2 drive rotation of the second end effector element 410 about the second yaw axis 408. FIGS. 4a and 4b also illustrate a third pair of driving elements C1, C2 which are constrained to move around pitch joint 401. Driving elements C1, C2 drive rotation of the end effector 303 about the pitch axis 402. The end effector 303 can be rotated about the pitch axis 402 by applying tension to driving elements C1 and/or C2. The pitch joint 401 and yaw joints 405, 407 are independently driven by their respective driving elements.

Figure 5:
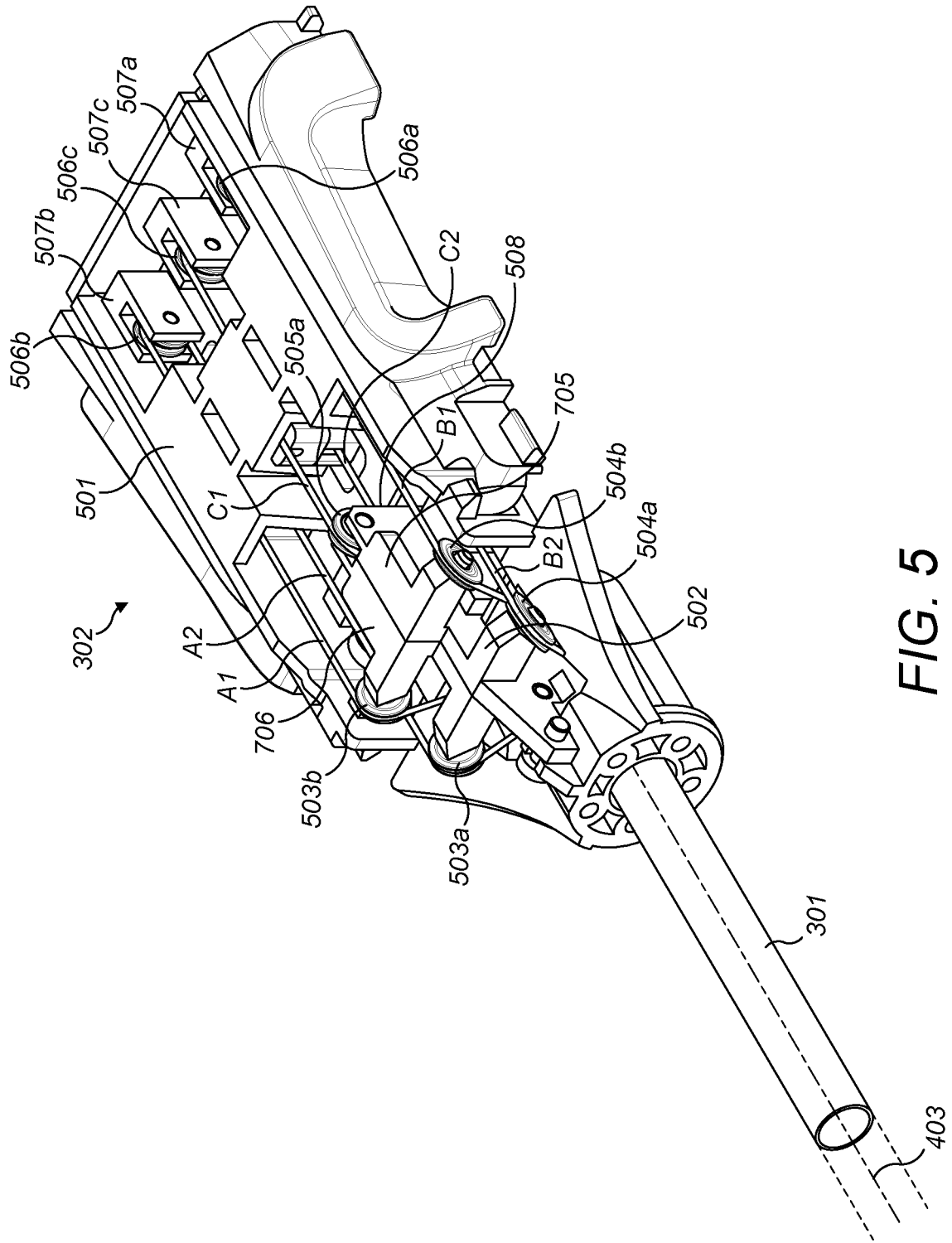
FIG. 5 illustrates the instrument interface at the proximal end of an exemplary surgical instrument.

FIG. 5 illustrates the instrument interface 302 at the proximal end of the surgical instrument attached to the shaft 301 of the instrument. The instrument interface 302 comprises a monocoque chassis 501 and a routing pulley component 502. Suitably, the monocoque chassis 501 is rigidly secured to the shaft of the instrument 301. The monocoque chassis 501 houses instrument interface elements 902 (visible in the cross section of FIG. 9). The instrument interface elements are exposed at the exterior of the instrument interface for engaging corresponding drive assembly interface elements of the robot arm. Each instrument interface element is secured to a respective driving element or pair of driving elements A1,A2, B1,B2, C1,C2. The routing pulley component comprises sets of pulleys 503, 504, 505. Driving elements A1,A2, B1,B2, C1,C2 from the shaft are routed around the sets of pulleys 503, 504, 505 to the instrument interface elements. The routing pulley component thereby routes each driving element from its position in the shaft to be aligned with its respective instrument interface element to which it is secured. Motion of the end effector is thereby driven by movement of the joints of the articulation 304, those joints being driven by movement of the driving elements A1,A2, B1,B2, C1,C2, those driving elements passing through the shaft and around the pulleys of the routing pulley component 502 to the instrument interface elements where they are driven by motion of the instrument interface elements, those instrument interface elements themselves being driven by drive assembly interface elements of the robot arm.

Figure 6:
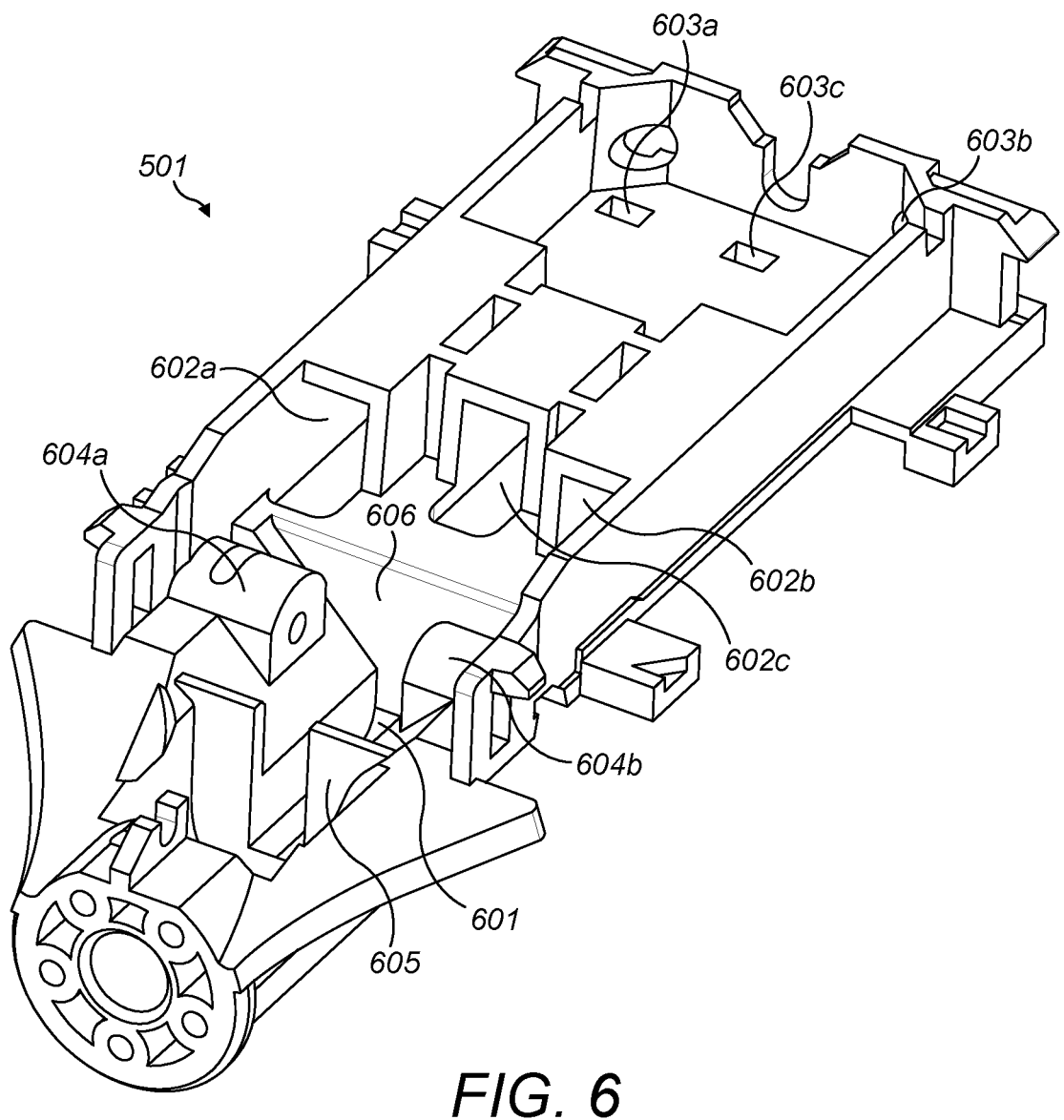
FIG. 6 illustrates a monocoque chassis of the instrument interface.

FIG. 6 illustrates the monocoque chassis 501 in isolation. The monocoque chassis is formed from a single piece only. This single piece connects the instrument shaft to the instrument interface elements. The monocoque chassis may be fabricated from metal, such as aluminium. Alternatively, the monocoque chassis may be fabricated from a plastic.

The monocoque chassis 501 has a recess 601 for receiving the routing pulley component. Recess 601 is shaped so as to retain the routing pulley component in position. Recess 601 is shaped so as to prevent relative lateral movement of routing pulley component and monocoque chassis in the plane of the instrument interface either parallel to the longitudinal axis 403 of the shaft or perpendicular to the longitudinal axis 403 of the shaft.

The monocoque chassis 501 also has recesses 602a,b,c, each one for receiving an instrument interface element. Each recess 602a,b,c comprises a channel along which its respective instrument interface element is displaceable when housed by the monocoque chassis 501. This channel is parallel to the line of the driving element through the instrument interface element. The channel is parallel to the longitudinal axis 403 of the shaft.

Figure 9:
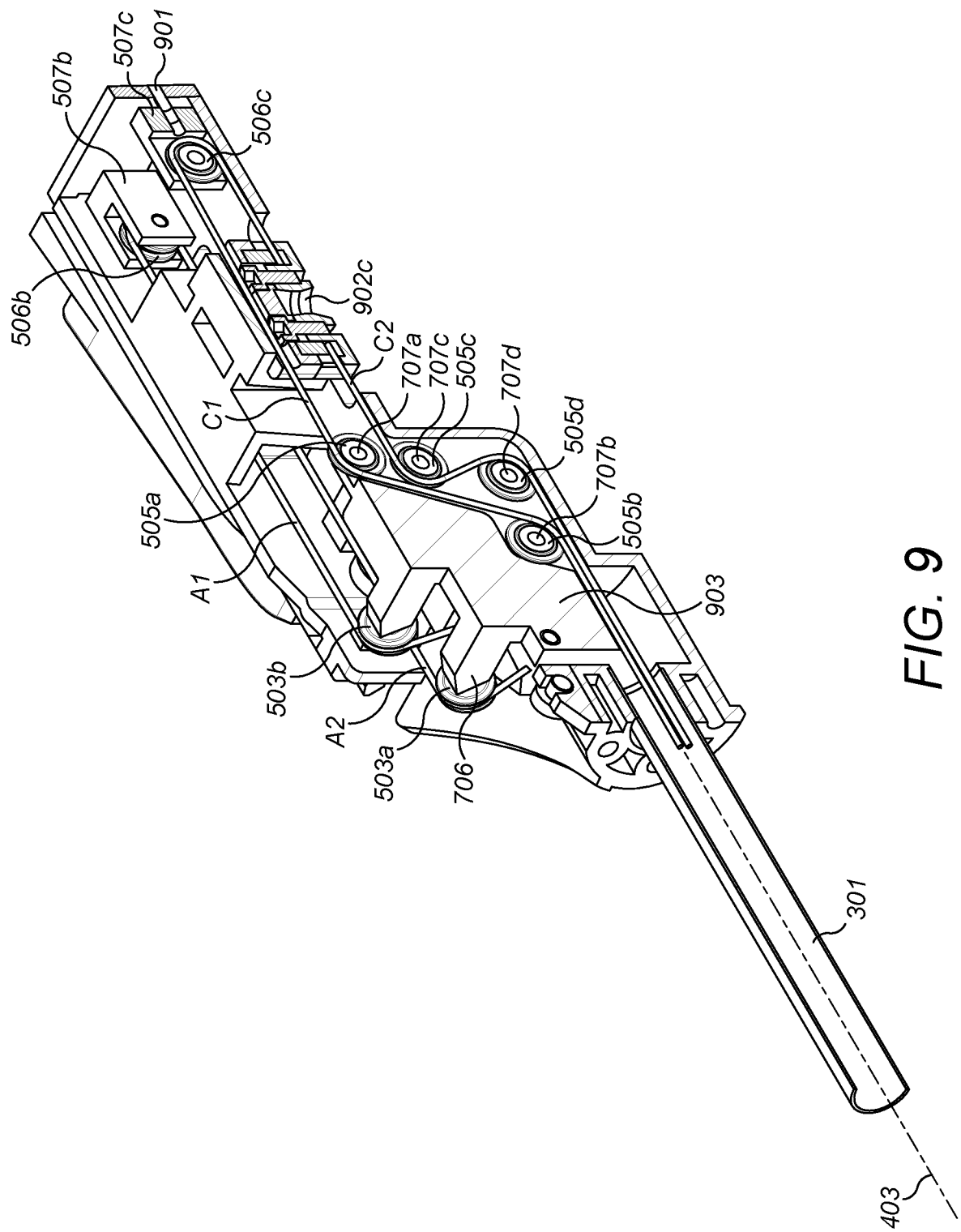
FIG. 9 illustrates a cross section of the instrument interface.

The monocoque chassis 501 further comprises features (such as cut outs 603a,b,c) to which a set of rear pulleys 506a,b,c may be attached, each rear pulley for constraining a driving element. Excluding the routing pulley component, suitably these rear pulleys are the only pulleys attached to the monocoque chassis which constrain the driving elements. These features and their associated pulleys are located at the opposing end of the instrument interface to the shaft. Each rear pulley acts to direct its associated driving element from where it is secured to the instrument interface element towards the shaft. In the instrument interface depicted, this is via a 180° directional change of the driving element from parallel to the longitudinal axis 403 of the shaft away from the shaft to parallel to the longitudinal axis 403 towards the shaft. This is easily seen on FIG. 9 for driving element C1,C2. Each rear pulley may be moveable so as to tension the driving element it constrains. For example, the rear pulleys may be displaceable parallel to the longitudinal axis 403 away from the shaft 301 so as to tension the captured driving element. FIG. 9 illustrates a mechanism for this, whereby the pulley casing 507a,b,c is displaceable parallel to the longitudinal axis 403 thereby displacing the encased rear pulley. In FIG. 9, the pulley casing 507a,b,c is slidable along a rail 901. Alternatively, a different motion of the rear pulley may be used to tension the driving element it constrains, such as a rotational motion.

FIGS. 7a and 7b illustrate the routing pulley component 502 in isolation. The routing pulley component 502 is separable from the monocoque chassis 501. The routing pulley component 502 may be fabricated from metal, such as aluminium. Alternatively, the routing pulley component 502 may be fabricated from a plastic. The routing pulley component 502 comprises two opposing external faces 701 and 702.

Figure 8A:
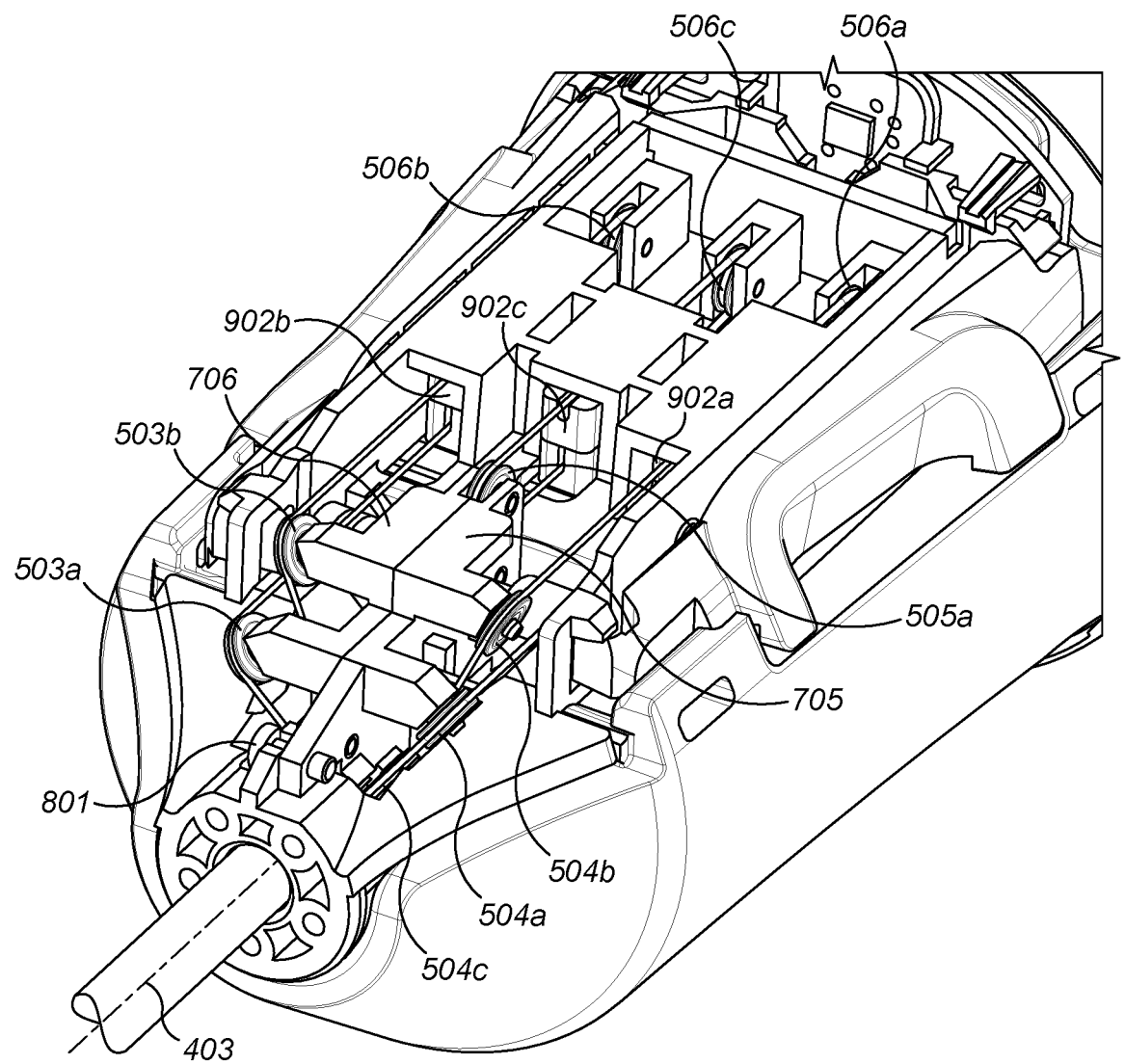
FIGS. 8a and 8b illustrate the instrument interface.
Figure 8B:
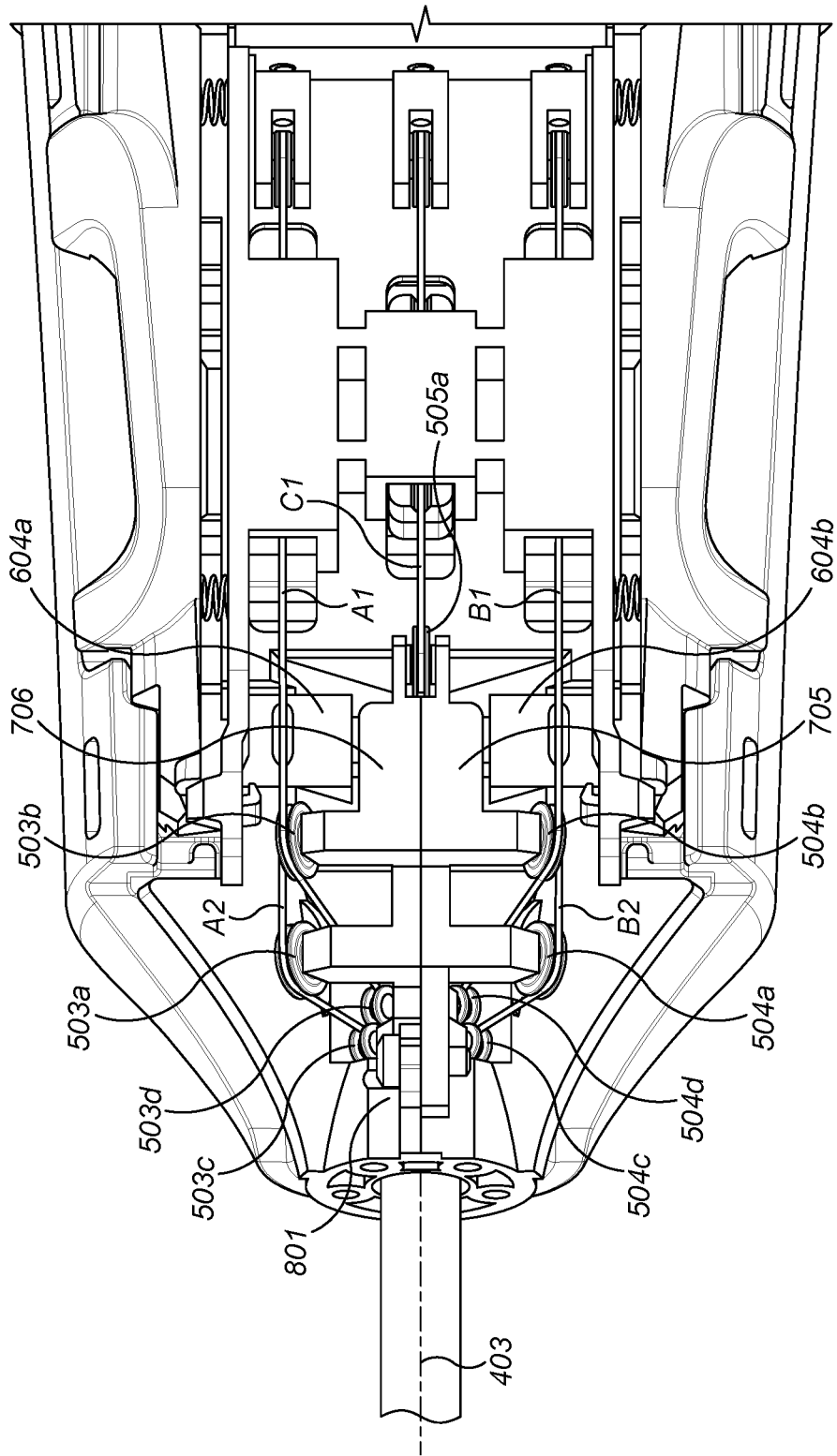

The first external face 701 comprises a first set of pulley mounts 703a,b,c,d onto which a first set of pulleys 504a,b,c,d are mounted. As shown in FIGS. 8a and 8b, once assembled in the instrument interface, these pulleys 504a,b,c,d constrain driving elements B1 and B2, directing them between the shaft and the instrument interface element 902a. Pulley mount 703a, and hence pulley 504b, is aligned with instrument interface element 902a such that the driving element B1 runs between pulley 504b and instrument interface element 902a parallel to the longitudinal axis 403 of the shaft. Pulley mount 703b, and hence pulley 504d, is aligned with shaft 301 such that the driving element B1 runs between pulley 504d and the shaft 301 parallel to the longitudinal axis 403 of the shaft. Pulley mount 703c, and hence pulley 504a, is aligned with instrument interface element 902a such that the driving element B2 runs between pulley 504a and instrument interface element 902a parallel to the longitudinal axis 403 of the shaft. Pulley mount 703d, and hence pulley 504c, is aligned with shaft 301 such that the driving element B2 runs between pulley 504c and the shaft 301 parallel to the longitudinal axis 403 of the shaft. Thus, the first external face 701 acts to route the driving elements B1 and B2 between the shaft and the instrument interface element 902a. The first set of pulley mounts 703a,b,c,d, and hence the first set of pulleys 504a,b,c,d, are aligned in a first plane. Thus, the driving elements B1 and B2 are also aligned in that first plane. The instrument interface element 902a is aligned in the same first plane. Additionally, the rear pulley 506a is aligned in the same first plane.

The second external face 702 comprises a second set of pulley mounts 704a,b,c,d onto which a second set of pulleys 503a,b,c,d are mounted. Once assembled in the instrument interface, these pulleys 503a,b,c,d constrain driving elements A1 and A2, directing them between the shaft and the instrument interface element 902b. Pulley mount 704a, and hence pulley 503b, is aligned with instrument interface element 902b such that the driving element A1 runs between pulley 503b and instrument interface element 902b parallel to the longitudinal axis 403 of the shaft. Pulley mount 704b, and hence pulley 503d, is aligned with shaft 301 such that the driving element A1 runs between pulley 503d and the shaft 301 parallel to the longitudinal axis 403 of the shaft. Pulley mount 704c, and hence pulley 503a, is aligned with instrument interface element 902b such that the driving element A2 runs between pulley 503a and instrument interface element 902b parallel to the longitudinal axis 403 of the shaft. Pulley mount 704d, and hence pulley 503c, is aligned with shaft 301 such that the driving element A2 runs between pulley 503c and the shaft 301 parallel to the longitudinal axis 403 of the shaft. Thus, the second external face 702 acts to route the driving elements A1 and A2 between the shaft and the instrument interface element 902b. The second set of pulley mounts 704a,b,c,d, and hence the second set of pulleys 503a,b,c,d, are aligned in a second plane. Thus, the driving elements A1 and A2 are also aligned in that second plane. The instrument interface element 902b is aligned in the same second plane. Additionally, the rear pulley 506b is aligned in the same second plane.

The routing pulley component may be composed of two separable sections 705 and 706 which are joined together during assembly of the instrument interface. The first section 705 comprises the first external face 701. The second section 706 comprises the second external face 702. The first section 705 comprises a first inner face opposing the first external face 701. The second section 706 comprises a second inner face 903 opposing the second external face 702. When the first and second sections 705 and 706 are joined together, the first and second inner faces interface each other. One or both of the first and second inner faces have a third set of pulley mounts 707a,b,c,d. In FIGS. 7a and 7b, pulley mount 707a is fully visible. Only the outsides of pulley mounts 707b,c,d are visible on the first and second external faces. A third set of pulleys 505a,b,c,d are mounted onto the third set of pulley mounts. Thus, once brought together, the first and second inner faces are joined so as to provide the third set of pulleys.

Once assembled in the instrument interface, the third set of pulleys 505a,b,c,d constrain driving elements C1 and C2, directing them between the shaft and the instrument interface element 902c. Pulley mount 707a, and hence pulley 505a, is aligned with instrument interface element 902c such that the driving element C1 runs between pulley 505a and instrument interface element 902c parallel to the longitudinal axis 403 of the shaft. Pulley mount 707b, and hence pulley 505b, is aligned with shaft 301 such that the driving element C1 runs between pulley 505b and the shaft 301 parallel to the longitudinal axis 403 of the shaft. Pulley mount 707c, and hence pulley 505c, is aligned with instrument interface element 902c such that the driving element C2 runs between pulley 505c and instrument interface element 902c parallel to the longitudinal axis 403 of the shaft. Pulley mount 707d, and hence pulley 505d, is aligned with shaft 301 such that the driving element C2 runs between pulley 505d and the shaft 301 parallel to the longitudinal axis 403 of the shaft. Thus, the inner faces of the routing pulley component act to route the driving elements C1 and C2 between the shaft and the instrument interface element 902c. The third set of pulley mounts 707a,b,c,d, and hence the third set of pulleys 505a,b,c,d, are aligned in a third plane. Thus, the driving elements C1 and C2 are also aligned in that third plane. The instrument interface element 902c is aligned in the same third plane. Additionally, the rear pulley 506c is aligned in the same third plane.

Alternatively, the routing pulley component may be unitary. In other words, the routing pulley component may have a single body. In this case, the body of the routing pulley component may be formed with a central recess. This central recess enables the third set of pulleys to be fitted to the body, and the third set of driving elements C1,C2 to be routed through the recess around the third set of pulleys.

In the examples described above, the pulleys of the routing pulley component are mounted such that each driving element runs between the instrument shaft and the instrument interface element in a direction parallel to the longitudinal axis of the shaft. The pulleys of the instrument interface and the instrument interface element which constrain that driving element along with the driving element itself are all aligned in the same plane in the instrument interface. In an alternative arrangement, the pulleys of the routing pulley component may be mounted at an angle to the longitudinal axis of the shaft. For example, they may be mounted perpendicular to the longitudinal axis of the shaft. In this example, each driving element changes direction as it is routed from the shaft via the routing pulley component to the instrument interface element. Thus, the direction of the driving element is not retained parallel to the longitudinal axis of the shaft. In this case, the pulleys of the instrument interface and the instrument interface element which constrain that driving element and the driving element itself are not aligned in the same plane in the instrument interface. Each driving element is not retained in a single plane.

FIG. 5 illustrates the instrument interface in an assembled state in which the routing pulley component 502 is housed by the monocoque chassis 501. FIGS. 8a, 8b and 9 also illustrate the instrument interface when the routing pulley component 502 is housed by the monocoque chassis 501. FIG. 9 shows a cross section of the instrument interface. That cross section is taken in a plane parallel to, and intersecting, the longitudinal axis 403 of the instrument shaft 301 such that the third set of pulleys of the routing pulley component 502 are visible.

In the examples shown in the figures, the routing pulley component 502 and the monocoque chassis 501 are shaped and sized such that the routing pulley component 502 push fits into the monocoque chassis 501. In other words, the routing pulley component 502 fits snuggly into the monocoque chassis 501 such that lateral movement in the plane of the instrument interface is minimised. To achieve this, the monocoque chassis of the figures comprises features which abut portions of the routing pulley component. For example, nibs 604a and 604b abut the first and second external faces 701 and 702. As a further example, front retaining wall 605 abuts the front face 708 of the routing pulley component, the front face 708 being transverse to the first and second external faces 701 and 702. As a further example, rear retaining wall 606 abuts the rear face 508 of the routing pulley component, the rear face 508 being transverse to the first and second external faces 701 and 702.

The routing pulley component may be secured to the monocoque chassis by a fixing. Suitably, only a single fixing is used to secure the routing pulley component to the monocoque chassis. For example, a screw or nut and bolt 801 may be used. In the case that the routing pulley component push fits into the monocoque chassis, as described above, the single fixing is located so as to resist vertical movement of the routing pulley component, perpendicular to the plane of the instrument interface. As described above, lateral movement within the plane of the instrument interface is resisted by the close fit between the routing pulley component and the monocoque chassis. Additionally or alternatively, the tension of the driving elements routed around the routing pulley component retain the routing pulley component pressed against the monocoque chassis. This acts to resist relative movement of the routing pulley component and the monocoque chassis.

Figure 10:
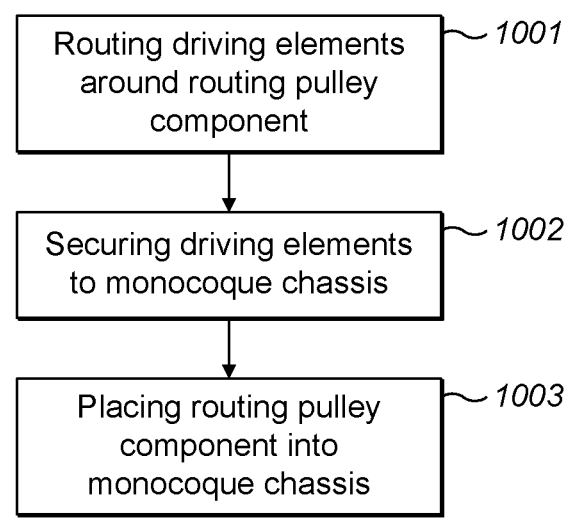
FIG. 10 is a flowchart illustrating a method of assembling the instrument interface.

FIG. 10 illustrates a method of assembling the instrument interface of the robotic surgical instrument described herein. Suitably, the driving elements are constrained around the joints and pulleys of the articulation at the distal end of the instrument and fed through the shaft to the instrument interface prior to the steps of FIG. 10. Alternatively, the instrument interface may be assembled first, and then the driving elements fed through the shaft to the articulation where they are constrained.

At step 1001, the driving elements are routed around the pulleys of the routing pulley component. Referring to FIGS. 7 and 8, this may be implemented by: (i) routing driving elements B1 and B2 around the first set of pulleys 504a,b,c,d on the first external face of the routing pulley component, (ii) routing driving elements A1 and A2 around the second set of pulleys 503a,b,c,d on the second external face 702 of the routing pulley component, and (iii) routing driving elements C1 and C2 around the third set of pulleys 505a,b,c,d of the routing pulley component.

In the example that the routing pulley component is formed of two sections 705 and 706, step 1001 may be implemented by, whilst the first section 705 is separated from the second section 706 with the third set of pulleys 505a,b,c,d attached to one of the inner faces of the first and second section: (i) routing driving elements C1 and C2 around the third set of pulleys 505a,b,c,d, then (ii) joining the first and second sections together by joining the second inner face of the second section to the first inner face of the first section so as to constrain the driving elements C1 and C2 around pulleys 505a,b,c,d between the first and second sections, then (iii) routing driving elements A1 and A2 and B1 and B2 around the pulleys of the first and second external faces as described above.

At step 1002, the driving elements are secured to the monocoque chassis. In the example shown in FIG. 9, step 1002 may be implemented in respect of driving element C1 by: (i) routing the driving element C1 through the recess 602c in the monocoque chassis for holding the instrument interface element 902c, (ii) routing the driving element C1 around the rear pulley 506c, and (iii) securing the driving element C1 to the instrument interface element 902c. Step 1002 may be implemented in respect of driving element C2 by: securing the driving element C2 to the instrument interface element 902c. A corresponding implementation may be carried out for the other driving elements of the instrument.

At step 1003, the routing pulley component is placed into the monocoque chassis. Suitably, the routing pulley component push fits into the monocoque chassis.

The assembly method may further comprise securing the routing pulley component to the monocoque chassis by a single fixing, such as a screw or nut and bolt 801 as described above.

Once the routing pulley component is housed in the monocoque chassis, the assembly method may further comprise tensioning each driving element by moving the rear pulley 506 about which that driving element is constrained. For example, the rear pulley 506 may be displaced away from the shaft to tension the driving element. This displacement may be parallel to the longitudinal axis 403 of the shaft as described above. Alternatively, the rear pulley 506 may be rotated so as to spool the driving element thereby tensioning the driving element.

Once the routing pulley component is housed in the monocoque chassis, and the driving elements tensioned, then a casing may be placed over the monocoque chassis to complete assembly of the instrument interface.

In the assembly method described above, step 1002 follows step 1001. However, alternatively step 1001 may follow step 1002, or both steps 1001 and 1002 may be performed concurrently. In the assembly method described above, step 1003 is implemented after steps 1001 and 1002. Step 1003 may only be performed after step 1001. However, in an alternative method, step 1003 may be performed prior to step 1002.

The instrument interface described above uses a monocoque chassis. In other words, the body which houses all the instrument interface elements which drive the driving elements is formed of a single part. A chassis formed in a single part in this way provides additional rigidity to the instrument interface compared to the two-part chassis previously used.

Thus, the flex in the chassis is significantly reduced, and hence the mechanical drive to the end effector is more efficient with fewer frictional losses. A rigid chassis resists tension forces deforming the chassis. Such deformation contributes to the misalignment of the drive direction and shaft direction. Chassis deformation also reduces the precision and control over the tension of the driving elements. This is because deformation of the part of the chassis which houses one driving element may affect the tension of the other driving elements which are attached to the same chassis. By utilising a single part chassis, chassis deformation is significantly reduced.

Use of a separable routing pulley component which push fits into the monocoque chassis with at most a single securing fixing simplifies the assembly of the instrument interface. It is quicker and more straightforward to feed the driving elements through the routing pulley component and then house the routing pulley component into the monocoque chassis than the assembly with a two-component chassis.

There are fewer component parts of the instrument interface overall with the apparatus described herein. This, combined with the simpler assembly, leads to an improved DFMA (Design for Manufacture and Assembly).

As described above, each set of pulleys of the routing pulley component is preferably mounted in the same plane as the instrument interface element it routes the associated driving element to. Ideally, the rear pulley of the monocoque chassis, if used, is also mounted in this same plane. This alignment reduces sliding friction and drag caused by the driving elements rubbing on the pulleys in the instrument interface. Thus, this alignment provides a more efficient mechanical drive transfer from the instrument interface element to the end effector. In the alternative implementation described above in which each set of pulleys of the routing pulley component is mounted at an angle to the instrument interface element it routes the associated driving element to, a more compact instrument interface design is enabled. In other words, this implementation enables the instrument interface elements to be closer to the instrument shaft.

As mentioned above, each of the monocoque chassis and routing pulley component may be fabricated from a metal or plastic. Use of a metal, in particular for the monocoque chassis, improves tensioning of the driving elements during autoclave cycles following use of the instrument.

The driving elements may be cables. The driving elements may comprise flexible portions and a rigid portion. Flexible portions engage the components of the instrument interface and the instrument articulation, and the rigid portion extends through all or part of the instrument shaft. For example, the flexible portion may be a cable, and the rigid portion may be a spoke. Other rigid portion(s) may be in the instrument interface or instrument articulation. For example, rack and pinions may be in the instrument interface or instrument articulation. The pair of driving elements which drive a joint of the articulation may be a cable loop. For example, A1 and A2 may be a single cable loop. In this case, the cable loop is attached to the joint in the articulation that it drives, for example by crimping. Alternatively, the pair of driving elements which drive a joint of the articulation may be two individual cables. For example, A1 may be a separate cable to A2. In this case, each cable is individually attached to the joint in the articulation that it drives, for example by crimping.

The robot described herein could be for purposes other than surgery. For example, the port could be an inspection port in a manufactured article such as a car engine and the robot could control a viewing tool for viewing inside the engine.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A robotic surgical instrument comprising:
    a shaft;
    driving elements running through the shaft;
    an articulation at a distal end of the shaft for articulating an end effector, the articulation driveable by the driving elements; and
    an instrument interface at a proximal end of the shaft for driving the driving elements, the instrument interface comprising:
       a monocoque chassis formed of a single piece only;
       instrument interface elements housed by the monocoque chassis, each instrument interface element being exposed at the exterior of the instrument interface so as to be driveable by a drive assembly external to the instrument interface, each driving element terminating at a corresponding instrument interface element; and
       a routing pulley component onto which pulleys for constraining the driving elements are mounted, the routing pulley component being housed by the monocoque chassis and separable from the monocoque chassis;
    wherein the instrument interface is configured to be assembled by:
       routing the driving elements around the pulleys of the routing pulley component;
       securing the driving elements to the monocoque chassis; and
       fitting the routing pulley component and the monocoque chassis together.

2. A robotic surgical instrument as claimed in claim 1, wherein the routing pulley component and monocoque chassis are shaped and sized such that the routing pulley component push fits into the monocoque chassis.

3. A robotic surgical instrument as claimed in claim 1, wherein the routing pulley component is secured to the monocoque chassis by a single fixing only.

4. A robotic surgical instrument as claimed in claim 1, wherein the routing pulley component comprises a first external face, the first external face comprising a first set of pulleys for constraining a first driving element, wherein a first joint of the articulation is driveable by the first driving element.

5. A robotic surgical instrument as claimed in claim 4, wherein the first set of pulleys are aligned in a first plane such that the first driving element lies in the first plane.

6. A robotic surgical instrument as claimed in claim 4 wherein the routing pulley component comprises a second external face, the second external face comprising a second set of pulleys for constraining a second driving element, wherein a second joint of the articulation is driveable by the second driving element, and wherein the routing pulley component comprises:
- a first section comprising the first external face; and
- a second section comprising the second external face;
- wherein the first section and second section are separable from each other.

7. A robotic surgical instrument as claimed in claim 6, wherein:
- the first section comprises a first inner face opposing the first external face; and
- the second section comprises a second inner face opposing the second external face;
- one or both of the first and second inner faces comprises a set of pulley mounts, the first and second inner faces being joinable together so as to provide a third set of pulleys on the set of pulley mounts for constraining a third driving element, wherein a third joint of the articulation is driveable by the third driving element.

8. A robotic surgical instrument as claimed in claim 1, wherein the routing pulley component comprises a second external face, the second external face comprising a second set of pulleys for constraining a second driving element, wherein a second joint of the articulation is driveable by the second driving element.

9. A robotic surgical instrument as claimed in claim 8, wherein the second set of pulleys are aligned in a second plane such that the second driving element lies in the second plane.

10. A robotic surgical instrument as claimed in claim 1 wherein the routing pulley component comprises a first external face, the first external face comprising a first set of pulleys for constraining a first driving element, wherein a first joint of the articulation is driveable by the first driving element, wherein the instrument interface element corresponding to a driving element lies in the same plane as the set of pulleys which constrains that driving element.

11. A robotic surgical instrument as claimed in claim 1, wherein for each driving element, the monocoque chassis comprises a single pulley only for constraining that driving element, the single pulley moveable so as to tension the driving element.

12. A robotic surgical instrument as claimed in claim 1, wherein the instrument interface is configured to be assembled by fitting the routing pulley component and the monocoque chassis together after routing the driving elements around the pulleys of the routing pulley component.

13. A method of assembling a robotic surgical instrument, the robotic surgical instrument comprising a shaft, driving elements, an articulation at the distal end of the shaft for articulating an end effector, the articulation driveable by the driving elements, and an instrument interface at a proximal end of the shaft for driving the driving elements, the instrument interface comprising a monocoque chassis formed of a single piece only, instrument interface elements housed by the monocoque chassis, each instrument interface element being exposed at the exterior of the instrument interface so as to be driveable by a drive assembly external to the instrument interface, each driving element terminating at a corresponding instrument interface element, and a routing pulley component onto which pulleys for constraining the driving elements are mounted, the routing pulley component being housed by the monocoque chassis and separable from the monocoque chassis, the method comprising:
- routing the driving elements around the pulleys of the routing pulley component;
- securing the driving elements to the monocoque chassis; and
- fitting the routing pulley component and the monocoque chassis together.

14. A method of assembling a robotic surgical instrument as claimed in claim 13, wherein the routing step comprises:
- routing a first driving element around a first external face of the routing pulley component; and
- routing a second driving element around a second external face of the routing pulley component.

15. A method of assembling a robotic surgical instrument as claimed in claim 14, wherein the routing pulley component comprises a first section and a second section, the first section comprising the first external face and a first inner face opposing the first external face, and the second section comprising the second external face and a second inner face opposing the second external face, wherein the first section and second section are separable from each other and one or both of the first and second inner faces comprises a set of pulley mounts, the routing step comprising:
- routing a third driving element around the first inner face of the first section; and
- joining the first and second sections together by joining the second inner face of the second section to the first inner face of the first section so as to constrain the third driving element about a set of pulleys on the set of pulley mounts provided by the joining together of the first and second sections.

16. A method of assembling a robotic surgical instrument as claimed in claim 13, wherein placing the routing pulley component into the monocoque chassis comprises push-fitting the routing component into the monocoque chassis.

17. A method of assembling a robotic surgical instrument as claimed in claim 13, further comprising securing the routing pulley component into the monocoque chassis by a single fixing only.

18. A method of assembling a robotic surgical instrument as claimed in claim 13, wherein for each driving element, the monocoque chassis comprises a single pulley only for constraining that driving element, the method further comprising tensioning each driving element by displacing the single pulley.

19. A method of assembling a robotic surgical instrument as claimed in claim 13, wherein fitting the routing pulley component and the monocoque chassis together is performed after routing the driving elements around the pulleys of the routing pulley component.

* * * * *